US009824561B2

(12) United States Patent
Brigham et al.

(10) Patent No.: US 9,824,561 B2
(45) Date of Patent: Nov. 21, 2017

(54) LOW POWER DETECTION AND ALARM

(71) Applicant: Sprue Safety Products, Ltd., Conventry (GB)

(72) Inventors: Peter Brigham, Conventry (GB); Stuart Hart, Conventry (GB)

(73) Assignee: Sprue Safety Products, Ltd., Coventry (GB)

( * ) Notice: Subject to any disclaimer, the term of this patent is extended or adjusted under 35 U.S.C. 154(b) by 0 days.

(21) Appl. No.: 14/443,187

(22) PCT Filed: Nov. 19, 2013

(86) PCT No.: PCT/GB2013/053049
§ 371 (c)(1),
(2) Date: May 15, 2015

(87) PCT Pub. No.: WO2014/080193
PCT Pub. Date: May 30, 2014

(65) Prior Publication Data

US 2015/0294546 A1 Oct. 15, 2015

(30) Foreign Application Priority Data

Nov. 20, 2012 (GB) .................................. 1220880.7

(51) Int. Cl.
*G08B 17/10* (2006.01)
*G08B 21/16* (2006.01)
(Continued)

(52) U.S. Cl.
CPC ............. *G08B 17/10* (2013.01); *G08B 21/12* (2013.01); *G08B 21/16* (2013.01); *G08B 29/181* (2013.01); *G08B 17/113* (2013.01)

(58) Field of Classification Search
CPC ......... G08B 17/00; G08B 17/10–17/11; G08B 17/107; G08B 29/181; G08B 21/12–21/16
See application file for complete search history.

(56) References Cited

U.S. PATENT DOCUMENTS

| | | | | |
|---|---|---|---|---|
| 3,314,058 A * | 4/1967 | Osborne | .............. | G08B 17/103 340/507 |
| 4,037,206 A * | 7/1977 | Dobrzanski | .......... | G08B 17/113 340/629 |

(Continued)

FOREIGN PATENT DOCUMENTS

| | | |
|---|---|---|
| CN | 201549047 U | 8/2010 |
| CN | 102063774 A | 5/2011 |

(Continued)

OTHER PUBLICATIONS

Great Britain Office Action dated Mar. 27, 2015 for Great Britain application No. GB1220880.7.

(Continued)

*Primary Examiner* — Orlando Bousono
(74) *Attorney, Agent, or Firm* — Ohlandt, Greeley, Ruggiero & Perle, LLP

(57) ABSTRACT

An alarm apparatus, for detecting radiation and/or pollutants including smoke and carbon monoxide, comprises an alarm circuit including a detector for radiation and/or pollutants and an audible alarm emitting device. A power supply circuit, connectable to an external AC power supply, supplies power to the alarm circuit. A controller operates the power supply circuit in a first mode of operation in which it supplies current to the alarm circuit at a first power level less than that required to energize the audible alarm emitting device and, in response to the detection of radiation and/or pollutants, operates the power supply in a second mode of operation in which it supplies current to the alarm circuit at a second power level sufficient to energize the audible alarm emitting device.

18 Claims, 8 Drawing Sheets

(51) Int. Cl.

| | |
|---|---|
| ***G08B 29/18*** | (2006.01) |
| ***G08B 21/12*** | (2006.01) |
| *G08B 17/113* | (2006.01) |

(56) References Cited

U.S. PATENT DOCUMENTS

| | | | | | |
|---|---|---|---|---|---|
| 4,038,649 | A * | 7/1977 | Dobrzanski | G08B 27/00 | 250/381 |
| 4,063,227 | A * | 12/1977 | Petersen | G08B 17/107 | 250/552 |
| 4,138,670 | A * | 2/1979 | Schneider | G01R 19/16542 | 340/333 |
| RE29,983 | E * | 5/1979 | Blackwell | G01R 19/16542 | 320/136 |
| 4,194,192 | A * | 3/1980 | Albinger, Jr. | G08B 13/00 | 340/517 |
| 4,196,426 | A * | 4/1980 | Ogawa | G08B 17/11 | 250/381 |
| 4,223,303 | A * | 9/1980 | Albinger, Jr. | G08B 17/00 | 340/531 |
| 4,223,305 | A * | 9/1980 | Arima | G08B 17/113 | 250/381 |
| 4,246,635 | A * | 1/1981 | Arima | H02M 3/07 | 363/101 |
| 4,300,099 | A * | 11/1981 | Maruyama | A62C 99/00 | 307/653 |
| 4,319,231 | A * | 3/1982 | Maruyama | G08B 17/00 | 340/509 |
| 4,511,889 | A * | 4/1985 | Atwater | G08B 17/10 | 250/384 |
| 4,524,304 | A * | 6/1985 | Todd | G08B 7/062 | 315/156 |
| 4,626,695 | A * | 12/1986 | Keeler | G08B 17/107 | 250/574 |
| 5,621,394 | A * | 4/1997 | Garrick | G08B 17/10 | 324/429 |
| 5,694,118 | A * | 12/1997 | Park | G01N 33/0063 | 340/628 |
| 5,966,002 | A | 10/1999 | Barrieau | | |
| 5,966,078 | A | 10/1999 | Tanguay | | |
| 6,157,307 | A * | 12/2000 | Hardin | G08B 21/20 | 340/604 |
| 6,439,891 | B1 * | 8/2002 | Tate | F16K 1/123 | 434/11 |
| 6,696,967 | B1 * | 2/2004 | Rutter | G08B 17/10 | 340/628 |
| 6,762,686 | B1 * | 7/2004 | Tabe | G08B 25/08 | 340/541 |
| 2006/0103540 | A1 * | 5/2006 | Rutter | G08B 17/00 | 340/628 |
| 2007/0132575 | A1 * | 6/2007 | Ellul | G08B 5/38 | 340/524 |
| 2008/0266121 | A1 * | 10/2008 | Ellul | G08B 7/066 | 340/584 |
| 2008/0303677 | A1 * | 12/2008 | Hart | G08B 17/10 | 340/600 |
| 2010/0188235 | A1 * | 7/2010 | Asano | G08B 17/107 | 340/578 |
| 2011/0121968 | A1 * | 5/2011 | Hart | G08B 7/06 | 340/540 |
| 2011/0304469 | A1 * | 12/2011 | Rutter | G08B 17/00 | 340/628 |

FOREIGN PATENT DOCUMENTS

| | | | |
|---|---|---|---|
| EP | 2693415 | A1 | 2/2014 |
| WO | 2010079336 | A1 | 7/2010 |

OTHER PUBLICATIONS

Great Britain Search Report dated Mar. 28, 2013 for Great Britain application No. GB1220880.7.

International Search Report dated Mar. 21, 2014 for PCT applciation No. PCT/GB2013/053049.

* cited by examiner

LOW POWER DETECTION AND ALARM

The present invention relates to an alarm apparatus and particularly, but not exclusively, to an alarm apparatus for detecting radiation and/or air pollutants such as smoke, carbon monoxide, radon and the like, and raising an alarm in response thereto.

Currently, AC powered alarms are designed to run either on AC with a non-rechargeable, replaceable backup battery or on AC with a rechargeable backup battery.

A disadvantage of this type of design is that the power supply circuit of the alarm, which rectifies the high voltage AC to a low voltage DC, must be able to supply sufficient current to the alarm to energise the alarm sounder when required (in the alarm condition). Where a rechargeable battery is provided, enough current must be supplied from the AC supply both to run the alarm sounder in an alarm condition and to charge the battery. This leads to a very energy inefficient alarm since, for most of the time, most of the power is simple wasted by the power supply circuit as heat as the power supply circuit is rated to supply a much greater current than is usually required during a normal sensing condition (as opposed to an alarming condition).

PCT application WO/2010/079336 goes some way to mitigating this problem, however as it relies on the battery to power the alarm sounder when it is in an alarming condition there is a dependence on the battery which is undesirable and, in some jurisdictions does not meet the required national standards for this type of device.

The present invention seeks to provide an improved alarm that at least partially mitigates problems associated with known alarm apparatus.

According to a first aspect of the invention there is provided an alarm apparatus for detecting radiation and/or pollutants including smoke and carbon monoxide, the apparatus comprising: an alarm circuit including detection means for detecting said radiation and/or pollutants and an audible alarm emitting device; a power supply circuit, connectable to an external AC power supply, that supplies power to said alarm circuit; a controller configured to operate the power supply circuit in a first mode of operation in which it supplies current to the alarm circuit at a first level less than that required to energise the audible alarm emitting device and, in response to the detection of said radiation and/or pollutants, to operate the power supply in a second mode of operation wherein it supplies current to the alarm circuit at a second level sufficient to energise the audible alarm emitting device.

Preferably the power supply circuit comprises a rectifier and a charge pump configured to reduce the voltage and increase the current from the rectifier. The charge pump is provided on the dc side of the rectifier to take the output from the rectifier which will have a voltage and a current, and to reduce the voltage and increase the current. Preferably the rectifier comprises a half wave rectifier.

Preferably the alarm apparatus comprises means, controlled by the controller, for controlling the voltage charge on a capacitor of the rectifier between a first voltage in the first mode of operation and a second, higher voltage in the second mode of operation. The means for controlling the voltage may comprises a thyristor, and the controller may be configured to supply a trigger current to the gate of the thyristor in the first mode of operation, and not to supply a trigger current to the gate of the thyristor in the second mode of operation.

In this manner the voltage charge that is built up on the capacitor of the rectifier is reduced in the first condition, as there is a voltage drop across the thyristor when a trigger is provided to its gate, and voltage charge that is built up on the capacitor of the rectifier is reduced in the second condition is increased as there is no voltage reduction across the thyristor and the full voltage is available to charge the capacitor of the rectifier. As the charge pump reduces voltage and increases current at a constant ratio (excluding power losses which are almost negligible) then the higher voltage available in the second mode of operation will result in a higher current being available in that second mode of operation for powering the alarm emitting device.

In one preferred arrangement power to drive the alarm circuit is taken from the power supply downstream of the charge pump. In an alternative preferred arrangement power to drive the alarm circuit is taken from the power supply from between the half wave rectifier and the charge pump.

The power supply circuit preferably comprises means for reducing the current supplied to said rectifier to a level below that required to energise said alarm, said means preferably comprising a capacitance in a power supply line of said power supply circuit. Preferably said capacitance comprises a plurality of capacitors in parallel. By using a plurality of capacitors in parallel the height of the space envelope of the capacitor(s) is reduced assisting in enabling a lower profile alarm apparatus.

The alarm apparatus preferably further comprises a battery for supplying power to said alarm circuit in the absence of AC power. Preferably a step up circuit is provided for increasing the voltage from the battery. In this way a lower voltage, for example a 3V lithium manganese dioxide cell can be used for powering the detection circuit and the stepped up voltage can be switched in to drive the alarm emitting device when the radiation or pollutants are detected. The switching of the step up circuit can be done by the controller, which may be a microcontroller.

According to a second aspect of the invention there is provided a method of providing power to an alarm apparatus for detecting radiation and/or pollutants including smoke and carbon monoxide, the method comprising: providing an alarm circuit including detection means for detecting said radiation and/or pollutants and an audible alarm emitting device; providing a power supply circuit, connectable to an external AC power supply, for supplying power to said alarm circuit; operating the power supply circuit in a first mode of operation in which it supplies current to the alarm circuit at a first level less than that required to energise the audible alarm emitting device and, in response to the detection of said radiation and/or pollutants, operating the power supply in a second mode of operation wherein it supplies current to the alarm circuit at a second level sufficient to energise the audible alarm emitting device.

Preferably providing a power supply circuit comprises providing rectifier and a charge pump, and increasing the current output from said rectifier with said charge pump. Preferably the method further comprises controlling the voltage charge of a capacitor of the rectifier between a first voltage in the first mode of operation and a second, higher voltage in the second mode of operation.

The method may further comprise: providing a thyristor, and supplying a trigger current to the gate of the thyristor in the first mode of operation, and not supplying a trigger current to the gate of the thyristor in the second mode of operation. Preferably the method further comprises reducing the current supplied to said rectifier to a level below that required to energise said alarm emitting device. In the event of detection of radiation and/or pollutants, the method may comprise increasing the current in the charge pump to a level sufficient to energise said alarm emitting device.

The method preferably further comprises providing a battery for supplying power to said alarm circuit in the absence of AC power. Preferably the battery has a voltage output below that required to energise the alarm emitting device and the method further comprises providing a step up circuit to increase the voltage from the battery.

An embodiment of the invention will now be described, by way of example. With reference to the following diagrams, in which.

Figure 1:
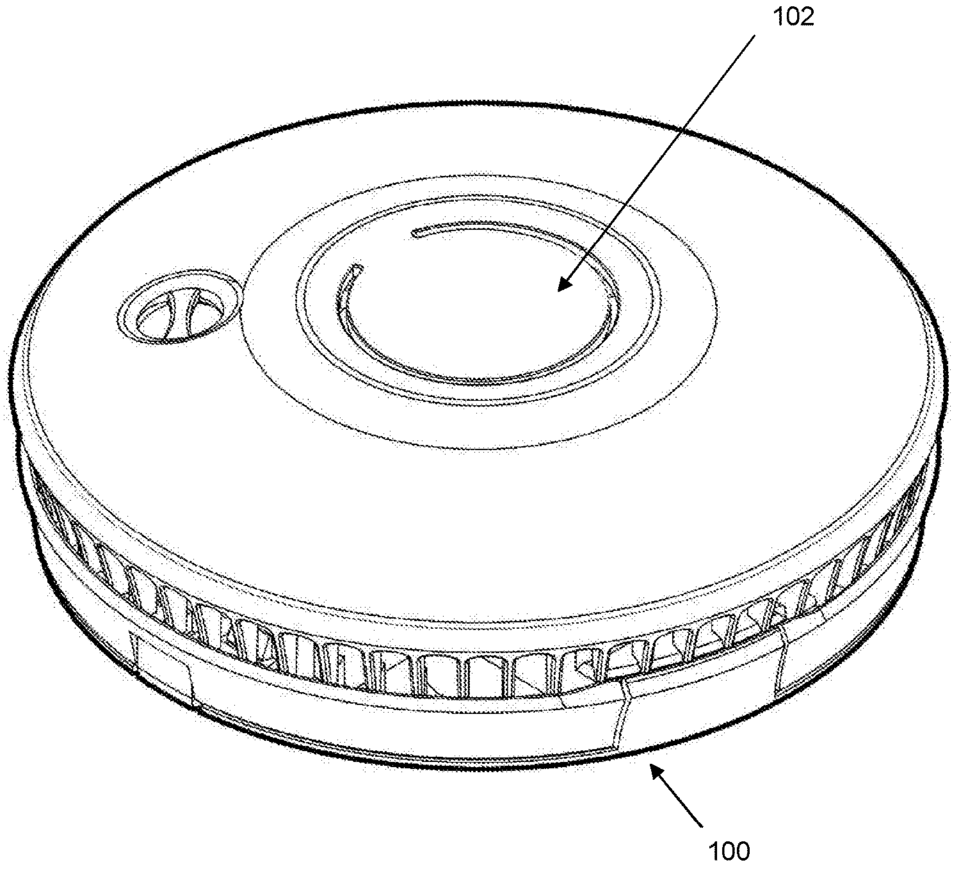
FIG. 1 is an alarm device in accordance with the invention.

FIG. 1 shows an alarm device 100 that detects radiation and/or pollutants including smoke and carbon monoxide. Within the alarm device is an alarm circuit that has detection means for detecting the radiation and/or pollutants and an audible alarm emitting device. A power supply circuit which is connectable to an external AC power supply supplies power to said alarm circuit and the Alarm device is provided with a controller which may be a microcontroller, for example a 162F1937 PIC controller from Microchip Technology Inc. The controller operates the power supply circuit in a first mode of operation in which it supplies current to the alarm circuit at a first level less than that required to energise the audible alarm emitting device. In this mode a low level of power is consumed during normal, operation, i.e. when the alarm device is not emitting the alarm. In response to the detection of radiation and/or pollutants, the controller operates the power supply in a second mode of operation in which it supplies current to the alarm circuit at a second level sufficient to energise the audible alarm emitting device.

Figure 2:
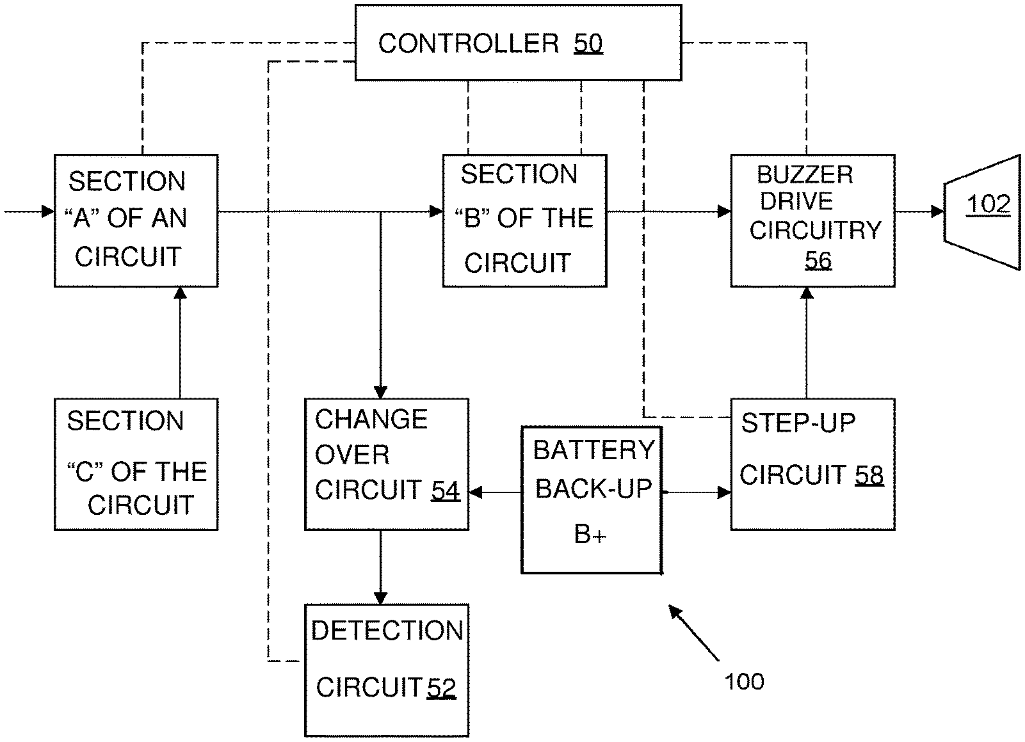
FIG. 2 shows a schematic diagram of the circuit of an alarm in accordance with the invention.

Referring to FIG. 2 a schematic of the electrical circuit of the alarm device is shown. A power supply section of the circuit comprises a first section "A" that receives an AC input and creates a variable DC voltage output at V high and V low, both at a substantially constant low current. The voltage level is controlled by a controller 50. A second part of the power supply section "B" receives the output from section "A" and reduces the voltage and increases the current, also under the control of the controller 50. A third section of circuitry "C" performs a safety function and controls the maximum voltage that can be output by section "A". The power from the power supply section of the circuit powers a detector circuit 52 via a change over circuit 54 which selects between powering the detector circuit with power from a battery B+ or the power supply section. If the detector circuit 52, which can be any known detector circuit as known in the art of smoke and fire detectors, detects a pollutant or radiation this is detected by the controller 50 which then powers a buzzer drive circuitry 56 that sounds the buzzer 102. Also provided for supplying power to the buzzer drive circuit is a battery step up circuit 58 that received power from the battery and increases its voltage to a suitable voltage to power the buzzer 102. The step up circuit 58 is controlled by the controller 50. The various sections of the circuit will be described below with reference to FIGS. 3 to 8.

Referring to FIGS. 3 to 6 the power supply circuit is provided with a first section "A" with connections L and GND for connection to live and neutral terminals of an AC power source, for example mains electricity. The current available from the AC source is reduced via two capacitors (10, 12) placed in parallel that reduce the current to a low level, in the region of 4 mA. The capacitors may be in the region of 100 nF. The low power side of the capacitors is connected to a half wave rectifier comprising diode 14, capacitor 16 and resistors 18, 19 wherein the AC voltage is transferred into DC voltage as is known in the art. The capacitor 16 may be in the region of 10 μF and the resistors 18, 19 in the region of 1 MΩ and 15 kΩ respectively. The DC output of the half wave rectifier is measured by the controller between the resistors 18 and 19. It will be appreciated that the symbol:

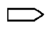

indicates a connection to the microcontroller.

Connected between the anode side of the diode 14 and ground there is provided a thyristor 20 having a gate feed provided by the microcontroller. Supply of a trigger signal to the gate of the thyristor 20 can cause or prevent a voltage drop across the thyristor. As will be appreciated, in the presence of a voltage drop across the thyristor 20 caused by a trigger signal, the capacitor 16 will charge to a lower voltage. In the absence of a trigger signal to the thyristor gate there will be no voltage drop across the thyristor 20 and the full voltage will be available to charge the capacitor which will therefore be charged to a higher voltage. Therefore, by supplying or not supplying a trigger signal from a microcontroller (omitted for clarity) to the gate of the thyristor 20 a low and a high voltage can be charged onto, and subsequently discharged from, the capacitor 16. Although described in relation to a half wave rectifier it will be well within the ability of the skilled person to apply this technique to a full wave rectifier. As described above this part of the circuit provides a low current (approximately 4 mA) power supply at two different voltages dependant upon a signal received from the microcontroller and part "A" of the circuit therefore provides a constant current variable voltage power supply.

The detection circuit 52 of the alarm apparatus needs a much smaller amount of power for driving it compared to the alarm emitting device, which may, for example, be a buzzer 102. As an example, a detection circuit 52 will typically run at approximately 3V and 10 μA and the buzzer will typically run at 30V and 12 mA, approximately 12,000 times the power consumption of the detection circuit.

In previous known alarm devices the power supply circuit has always been sized to the buzzer power requirements, resulting in a lot of wasted energy during conditions in which the buzzer is not sounding, which will be appreciated is the majority of the life of the device. These power losses are mainly through heat in the power supply circuit which is always capable of providing the full power requirement. Although the power savings may not seem great, based on current pricing patterns the power saving could equate to the cost of the device over the life of the alarm apparatus, thereby not only providing a more energy efficient device but making the device cost neutral in comparison to other devices.

Figure 3:
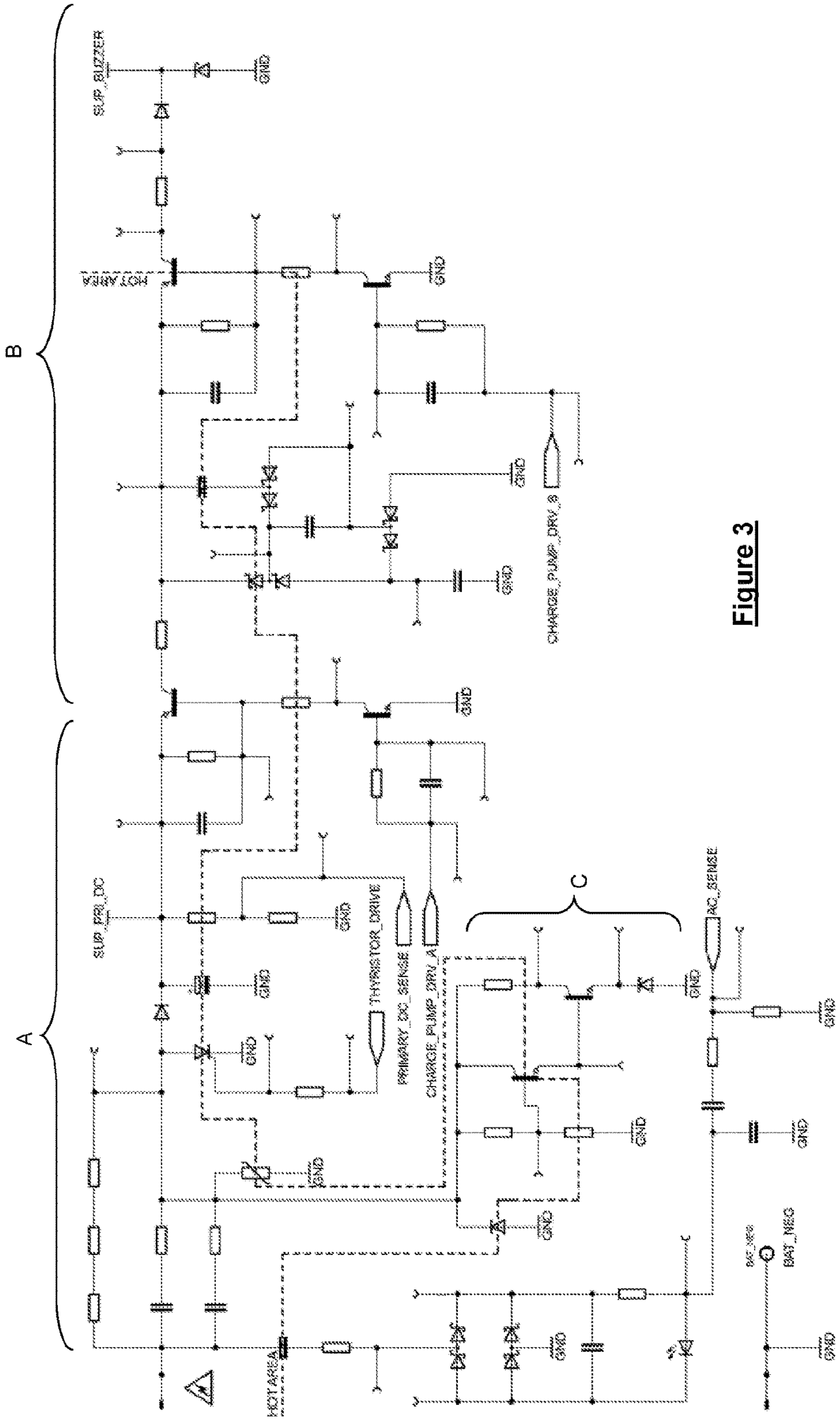
FIG. 3 is a circuit diagram for the power supply circuit in accordance with the invention.
Figure 4:
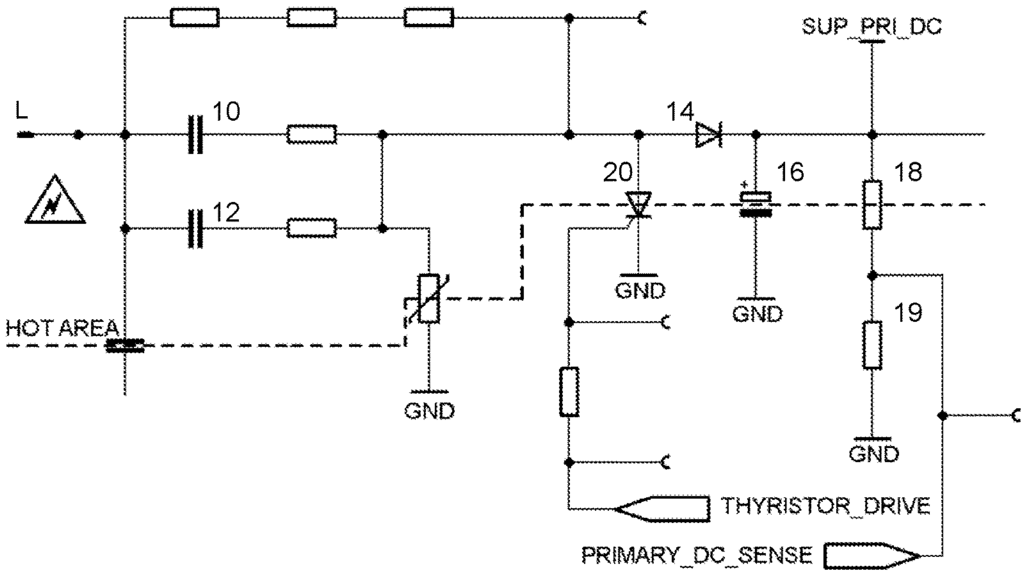
FIG. 4 shows section "A" of FIG. 2.
Figure 5:
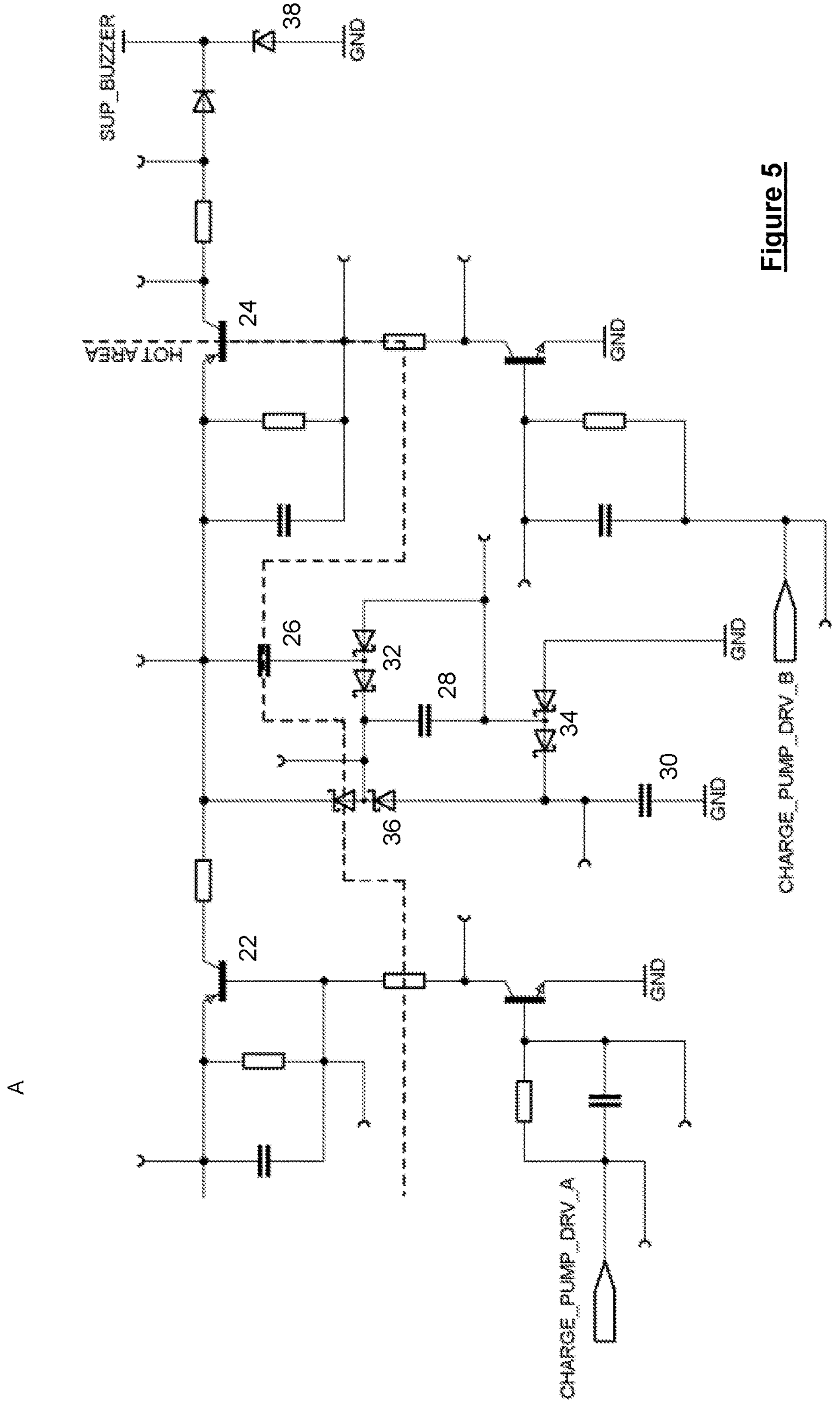
FIG. 5 shows section "B" of FIG. 2.

Referring to FIGS. 3 and 5 a second part of the power circuit B takes the output of the half wave rectifier and reduces its voltage and increases its current by passing it through a charge pump. Transistor 22 switches in the high voltage from the rectifier and transistor 24 switches out the low voltage from the charge pump, both under the control of the microcontroller. The charge pump operates as is known in the art, effectively through charging capacitors 26, 28, 30 in series, and discharging them in parallel, via a pairs of Schottky diodes 32, 34, 36. The capacitors may have each capacitances of 100 nF In the second mode of operation, in which the trigger signal to the thyristor 20 is not supplied, the capacitor 16 charges to approximately 90V and discharges with a current of approximately 4 mA. The charge pump alters the current/voltage balance to give an output of approximately 12 mA at 30V, which is sufficient to drive the buzzer. As in this method the input current draw is limited to approximately 4 mA, well below that required to directly drive the buzzer, smaller capacitors 10, 12 can be used which reduces the consequential power losses due to heat that would occur during the majority of the operational time if capacitors sized for a 12 mA current were used when only 4 mA was being drawn.

A zener diode 38 is provided between the buzzer input 40 and ground so that in the even of an excessive voltage there will be a leakage across the zener diode and the buzzer is therefore protected.

When the alarm device is in a detecting mode, the power for driving the detection circuit 52, which could be any known detection circuit, is provided from the power supply circuit at SUP_PRI_DC. As this is provided prior to the charge pump the current available at this point is approximately 4 mA and as the buzzer 102 is not operational there is no power drawn through the charge pump.

Figure 6:
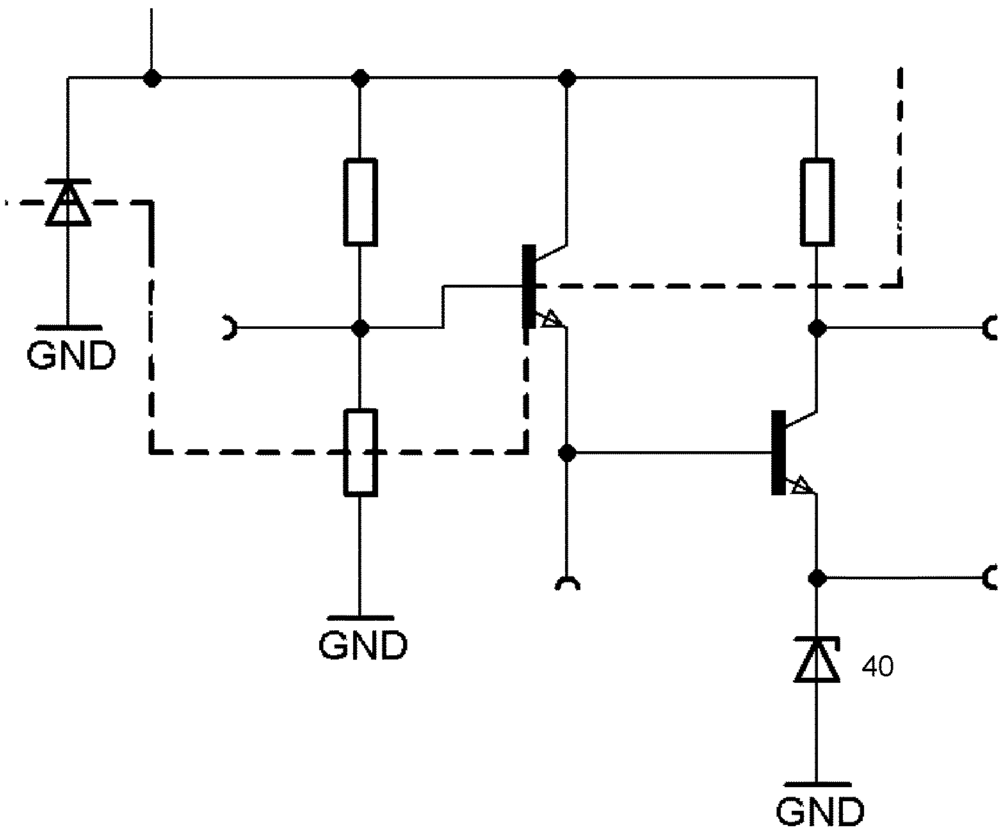
FIG. 6 shows section "C" of FIG. 1.

Referring in particular to FIG. 6 a third part "C" of the circuit is shown which is not directly related to the provision of the power, but provides a safety feature by controlling the maximum voltage that can be charged onto the capacitor 16 of the half wave rectifier. Should the voltage become too high the zener diode 40 will allow a drop across it restricting the maximum voltage available at the capacitor 16.

Figure 7:
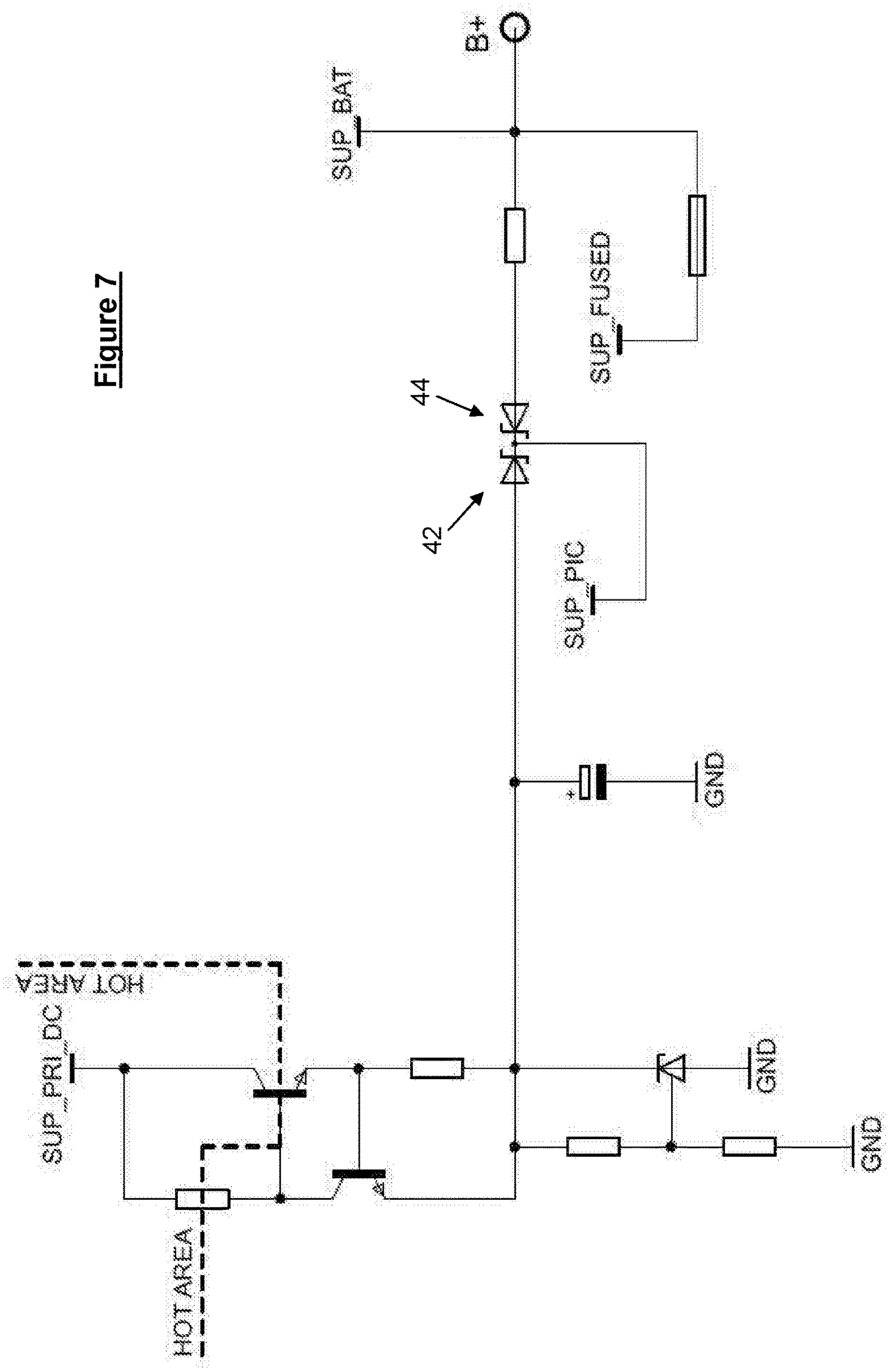
FIG. 7 is a circuit diagram of a power selection circuit for the detection circuit.

Referring to FIG. 7 a change over circuit 54 is shown which outputs power (SUP_PIC) for powering a detection circuit and which switches the power supply used to output that power between the supply from the power supply circuit (SUP_PRI_DC) and the battery back up B+, dependant on the power available from the power supply circuit. This is achieved via Schottky diodes 42, 44 such that when current is available at SUP_PRI_DC it will pass through diode 42 and to SUP_PIC and diode 44 will prevent a flow of current into the battery, and when current is not present at SUP_PRI_DC current will flow from the battery through diode 44 and to SUP_PIC and diode 42 will prevent a flow of current back through the mains power circuit. In this manner simple and effective switching between mains power and battery back up power is achieved when mains power is not available. A direct supply of power from the battery (SUP_FUSED) is also provided for supplying a supply of power from the battery B+ for powering the buzzer via a fuse 46 when operating in battery back up mode.

Figure 8:
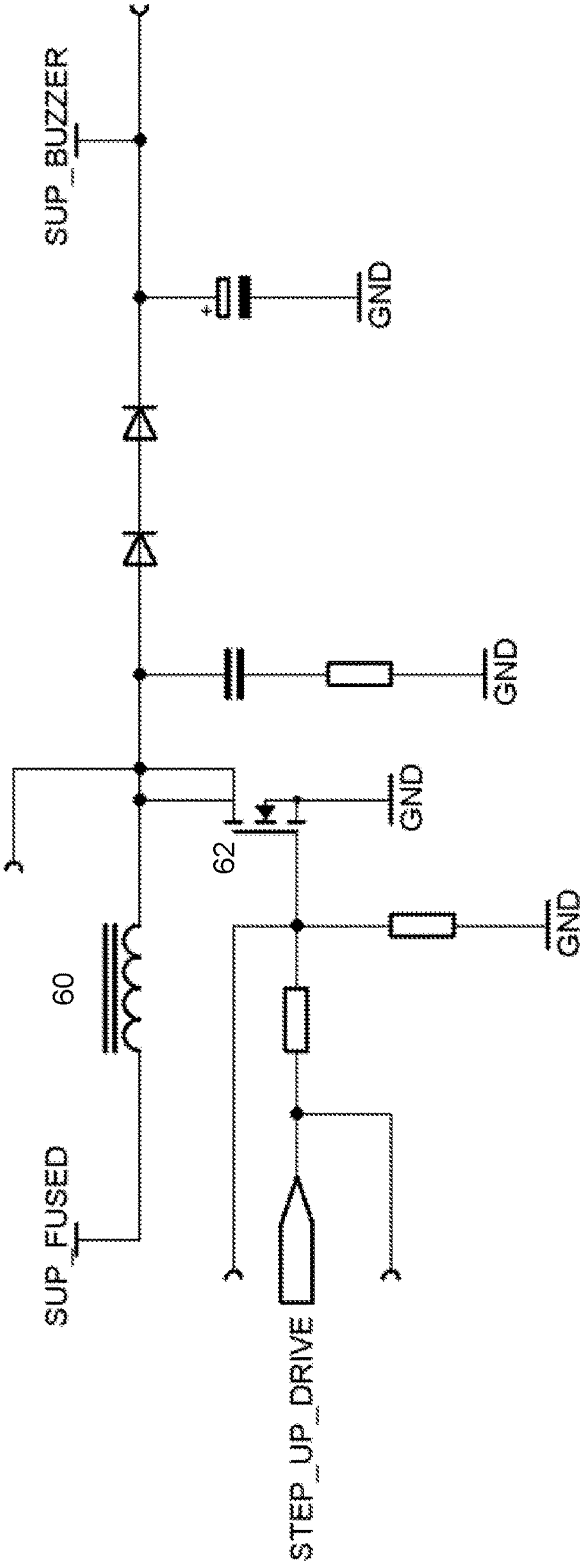
FIG. 8 is a circuit diagram for the battery step up circuit.

Referring to FIG. 8 the battery step up circuit 58 is shown. The fused supply (SUP_FUSED) from the battery passes through a inductor 60 wherein its voltage is increased to a voltage required to drive the buzzer, for example to approximately 30V. Control of the supply is achieved through an enhancement mode MOSFET transistor under the control of the controller 50.

What is claimed is:

1. An alarm apparatus for detecting radiation and/or pollutants including smoke and carbon monoxide, the apparatus comprising:

an alarm circuit including a detector for detecting said radiation and/or pollutants and an audible alarm emitting device;

a power supply circuit, connectable to an external AC power supply, including (a) a rectifying circuit configured to provide a rectified DC voltage power supply to said alarm circuit and (b) a current reducer for reducing the current supplied to the rectifying circuit so as to limit a current drawn from the AC power supply; and a controller configured to operate the power supply circuit in a first mode of operation in which it supplies current to the alarm circuit at a first power level less than that required to energize the audible alarm emitting device and, in response to the detection of said radiation and/or pollutants, to operate the power supply circuit in a second mode of operation wherein it supplies current from the AC power supply to the alarm circuit at a second power level sufficient to exclusively energize the audible alarm emitting device, wherein the rectifying circuit comprises a capacitor connected to the rectified DC voltage power supply and the power supply circuit includes a voltage controller, controlled by the controller, for controlling a voltage charge on said capacitor, wherein the capacitor is charged to a first voltage and maintained at the first voltage to provide current to the alarm circuit at the first power level in the first mode of operation and wherein the capacitor is charged to a second, higher voltage to provide current to the alarm circuit at the second power level in the second mode of operation.

2. The alarm apparatus according to claim 1, wherein the power supply circuit further comprises a charge pump configured to reduce the voltage and increase the current from the rectifying circuit.

3. The alarm apparatus according to claim 1, wherein the rectifying circuit comprises one of a half wave rectifier and a full wave rectifier.

4. The alarm apparatus according to claim 1, wherein the voltage controller comprises a thyristor, wherein the controller is configured to supply a trigger current to the gate of the thyristor in the first mode of operation, and wherein the controller is configured not to supply a trigger current to the gate of the thyristor in the second mode of operation.

5. The alarm apparatus according to claim 2, wherein power to drive the alarm circuit is taken from the power supply downstream of the charge pump.

6. The alarm apparatus according to claim 2, wherein power to drive the alarm circuit is taken from the power supply between the rectifying circuit and the charge pump.

7. The alarm apparatus according to claim 1, wherein said current reducer for reducing the current supplied to said rectifying circuit reduces the power to a level below that required to energize said alarm.

8. The alarm apparatus according to claim 7, wherein said current reducer comprises a capacitance in a power supply line of said power supply circuit.

9. The alarm apparatus according to claim 8, wherein said capacitance comprises a plurality of capacitors in parallel.

10. The alarm apparatus according to claim 1, further comprising a battery for supplying power to said alarm circuit in the absence of AC power.

11. The alarm apparatus according to claim 10, further comprising a step-up circuit for increasing the voltage from the battery.

12. A method of providing power to an alarm apparatus for detecting radiation and/or pollutants including smoke and carbon monoxide, the method comprising:

providing an alarm circuit including a detector for detecting said radiation and/or pollutants and an audible alarm emitting device;

providing a power supply circuit, connectable to an external AC power supply, wherein the power supply circuit includes a rectifying circuit configured to provide a rectified DC voltage power supply to said alarm circuit and further includes a current reducer for reducing the current supplied to the rectifying circuit so as to limit a current drawn from the AC power supply;

operating the power supply circuit in a first mode of operation in which it supplies current to the alarm circuit at a first power level less than that required to energize the audible alarm emitting device and, in response to the detection of said radiation and/or pollutants, operating the power supply circuit in a second mode of operation wherein it supplies current from the AC power supply to the alarm circuit at a second power level sufficient to exclusively energize the audible alarm emitting device, wherein providing a power supply circuit including a rectifying circuit comprises providing a capacitor connected to the rectified DC voltage power supply and controlling a voltage charge on said capacitor wherein the capacitor is charged to a first voltage and maintained at the first voltage to provide current to the alarm circuit at the first power level in the first mode of operation and wherein the capacitor is charged to a second, higher voltage to provide current to the alarm circuit at the second power level in the second mode of operation.

13. The method according to claim 12, wherein providing a power supply circuit further comprises providing a charge pump, and increasing the current output from said rectifying circuit with said charge pump.

14. The method according to claim 12, further comprising: providing a thyristor, and supplying a trigger current to the gate of the thyristor in the first mode of operation, and not supplying a trigger current to the gate of the thyristor in the second mode of operation.

15. The method according to claim 12, further comprising reducing the power supplied to said rectifying circuit to a level below that required to energize said alarm emitting device.

16. The method according to claim 15, further comprising, in the event of detection of radiation and/or pollutants, increasing the current in the charge pump to a level sufficient to energize said alarm emitting device.

17. The method according to claim 12, further comprising providing a battery for supplying power to said alarm circuit in the absence of AC power.

18. The method according to claim 17, wherein providing an battery comprises providing a battery having a voltage output below that required to energize the alarm emitting device and wherein the method further comprises providing a step-up circuit to increase the voltage from the battery.

* * * * *